US012020560B2

(12) United States Patent
Park et al.

(10) Patent No.: US 12,020,560 B2
(45) Date of Patent: Jun. 25, 2024

(54) DEVICE AND METHOD OF PROVIDING AUDIOVISUAL CONTENT FOR THE DISABLED

(71) Applicant: Samsung Electronics Co., Ltd., Suwon-si (KR)

(72) Inventors: Jaesung Park, Suwon-si (KR); Anant Baijal, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 89 days.

(21) Appl. No.: 17/951,728

(22) Filed: Sep. 23, 2022

(65) Prior Publication Data

US 2023/0169834 A1 Jun. 1, 2023

Related U.S. Application Data

(63) Continuation of application No. PCT/KR2022/001358, filed on Sep. 12, 2022.

(30) Foreign Application Priority Data

Nov. 30, 2021 (KR) .................. 10-2021-0168695

(51) Int. Cl.
*G08B 7/06* (2006.01)
*A61M 21/00* (2006.01)
(Continued)

(52) U.S. Cl.
CPC .............. *G08B 7/06* (2013.01); *A61M 21/00* (2013.01); *G06N 3/045* (2023.01); *G06N 3/08* (2013.01);
(Continued)

(58) Field of Classification Search
None
See application file for complete search history.

(56) References Cited

U.S. PATENT DOCUMENTS

| 2014/0356848 A1 | 12/2014 | Peterson |
| 2016/0165038 A1 | 6/2016 | Lim et al. |
| 2023/0024903 A1* | 1/2023 | Hong .................... G06F 16/904 |

FOREIGN PATENT DOCUMENTS

| KR | 10-2004-0022025 A | 3/2004 |
| KR | 10-2011-0103726 A | 9/2011 |

(Continued)

OTHER PUBLICATIONS

International Search Report dated Dec. 16, 2022, issued in International Patent Application No. PCT/KR2022/013585.

*Primary Examiner* — K. Wong
(74) *Attorney, Agent, or Firm* — Jefferson IP Law, LLP

(57) ABSTRACT

An electronic device is provided. The electronic device includes at least one processor, and at least one memory configured to store instructions executable by the at least one processor, wherein when the instructions are executed by the at least one processor, the at least one processor is configured to perform sensing an occurrence of a trigger event, based on an input to the electronic device and an input to at least one Internet of Things (IoT) device connected to the electronic device, collecting weather information in response to the occurrence of the trigger event, estimating an emotion of a user, based on at least one of context information stored for the user and the weather information, receiving, from the user, an audiovisual impairment state of the user or estimating the audiovisual impairment state based on the context information, determining audiovisual content for a disabled to output, based on at least one of the estimated emotion and the audiovisual impairment state, among the at least one IoT device, determining a target IoT device to output the determined audiovisual content for the disabled, and outputting the determined audiovisual content for the disabled through the target IoT device.

23 Claims, 6 Drawing Sheets

(51) Int. Cl.
    *G06N 3/045*         (2023.01)
    *G06N 3/08*           (2023.01)
    *G09B 21/00*         (2006.01)
    *H04L 67/12*         (2022.01)

(52) U.S. Cl.
    CPC ......... *G09B 21/006* (2013.01); *G09B 21/009* (2013.01); *H04L 67/12* (2013.01); *A61M 2021/0027* (2013.01); *A61M 2021/0044* (2013.01)

(56) References Cited

FOREIGN PATENT DOCUMENTS

| | | |
|---|---|---|
| KR | 10-2015-0097064 A | 8/2015 |
| KR | 10-1565727 B1 | 11/2015 |
| KR | 10-2017-0058600 A | 5/2017 |
| KR | 10-2018-0028939 A | 3/2018 |
| KR | 10-2018-0073167 A | 7/2018 |
| KR | 10-2019-0102151 A | 9/2019 |
| KR | 10-2020-0069506 A | 6/2020 |
| KR | 10-2020-0098180 A | 8/2020 |
| KR | 10-2208323 B1 | 1/2021 |
| KR | 10-2212638 B1 | 2/2021 |

\* cited by examiner

DEVICE AND METHOD OF PROVIDING AUDIOVISUAL CONTENT FOR THE DISABLED

CROSS-REFERENCE TO RELATED APPLICATION(S)

This application is a continuation application, claiming priority under § 365(c), of an International application No. PCT/KR2022/013585, filed on Sep. 12, 2022, which is based on and claims the benefit of a Korean patent application number 10-2021-0168695, filed on Nov. 30, 2021, in the Korean Intellectual Property Office, the disclosure of which is incorporated by reference herein in its entirety.

BACKGROUND

1. Field

The disclosure relates to a method of providing audiovisual content for a disabled.

2. Description of Related Art

An electronic device, such as an artificial intelligent speaker, may recommend or provide content on an image, music, food, and sports corresponding to context information by using context information on a user, such as a date, a day, time, weather, a birthday.

For example, the electronic device may express the weather by using content, such as lighting in a cool color in snowy weather, an image of snow falling, sound of stepping on snow, related music, and autonomous sensory meridian response (ASMR) content depending on the weather, and the user may identify the weather by watching and listening to the content.

The above information is presented as background information only to assist with an understanding of the disclosure. No determination has been made, and no assertion is made, as to whether any of the above might be applicable as prior art with regard to the disclosure.

SUMMARY

When the user has an audiovisual impairment, a user may have a sense that the user does not perceive depending on the audiovisual impairment. Even if an electronic device provides content on an image, music, food, and sports corresponding to context information on the user by using context information, the user may have a difficulty in completely perceiving the content.

Aspects of the disclosure are to address at least the above-mentioned problems and/or disadvantages and to provide at least the advantages described below. Accordingly, an aspect of the disclosure is to provide an electronic device and a method of providing audiovisual content for a disabled to provide a user with audiovisual impairment with emotional audiovisual content corresponding to the context, such as the weather, an environment, and a health condition of the user.

Additional aspects will be set forth in part in the description which follows and, in part, will be apparent from the description, or may be learned by practice of the presented embodiments.

In accordance with an aspect of the disclosure, an electronic device is provided. The electronic device includes at least one processor, and at least one memory configured to store instructions executable by the at least one processor, wherein, when the instructions are executed by the at least one processor, the at least one processor is configured to perform sensing an occurrence of a trigger event, based on an input to the electronic device and an input to at least one Internet of Things (IoT) device connected to the electronic device, collecting weather information in response to the occurrence of the trigger event, estimating an emotion of a user, based on at least one of context information stored for the user and the weather information, receiving, from the user, an audiovisual impairment state of the user or estimating the audiovisual impairment state based on the context information, determining audiovisual content for a disabled to output, based on at least one of the estimated emotion and the audiovisual impairment state, among the at least one IoT device, determining a target IoT device to output the determined audiovisual content for the disabled, and outputting the determined audiovisual content for the disabled through the target IoT device.

According to an embodiment, an electronic device and a method of providing audiovisual content for the disabled may estimate an emotion of a user, based on context information on the user with audiovisual impairment and may provide audiovisual content based on an audiovisual impairment state.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
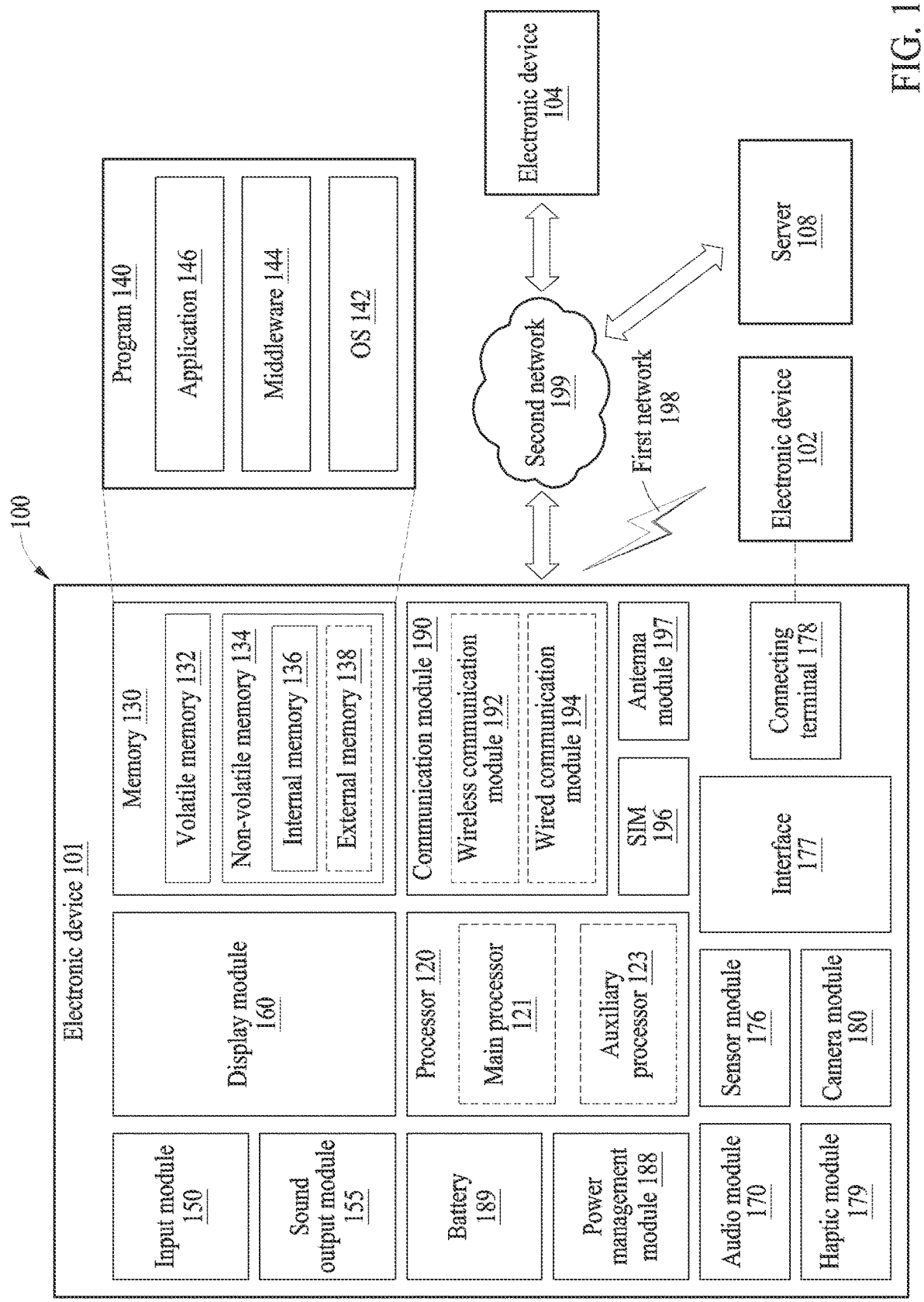
FIG. 1 is a block diagram illustrating an electronic device in a network environment according to an embodiment of the disclosure.

FIG. 1 is a block diagram illustrating an electronic device 101 in a network environment 100 according to an embodiment of the disclosure.

Referring to FIG. 1, an electronic device 101 in the network environment 100 may communicate with an electronic device 102 via a first network 198 (e.g., a short-range wireless communication network), or communicate with at least one of an electronic device 104 or a server 108 via a second network 199 (e.g., a long-range wireless communication network). According to an example embodiment, the electronic device 101 may communicate with the electronic device 104 via the server 108. According to another example embodiment, the electronic device 101 may include a processor 120, a memory 130, an input module 150, a sound output module 155, a display module 160, an audio module 170, and a sensor module 176, an interface 177, a connecting terminal 178, a haptic module 179, a camera module 180, a power management module 188, a battery 189, a communication module 190, a subscriber identification module (SIM) 196, or an antenna module 197. In some example embodiments, at least one of the components (e.g., the connecting terminal 178) may be omitted from the electronic device 101, or one or more other components may be added in the electronic device 101. In other example embodiments, some of the components (e.g., the sensor module 176, the camera module 180, the antenna module 197, and the like) may be integrated as a single component (e.g., the display module 160).

The processor 120 may be configured to execute, for example, software (e.g., a program 140) to control at least one other component (e.g., a hardware or software component) of the electronic device 101 connected to the processor 120, and may perform various data processing or computation. According to an example embodiment, as at least a part of data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to another example embodiment, the processor 120 may include a main processor 121 (e.g., a central processing unit (CPU) or an application processor (AP)), or an auxiliary processor 123 (e.g., a graphics processing unit (GPU), a neural processing unit (NPU)), an image signal processor (ISP), a sensor hub processor, or a communication processor (CP)) that may be operable independently from, or in conjunction with the main processor 121. For example, in a case in which the electronic device 101 includes the main processor 121 and the auxiliary processor 123, the auxiliary processor 123 may be adapted to consume less power than the main processor 121 or to be specific to a specified function. The auxiliary processor 123 may be implemented separately from the main processor 121 or as a part of the main processor 121.

The auxiliary processor 123 may control at least some of functions or states related to at least one (e.g., the display module 160, the sensor module 176, or the communication module 190) of the components of the electronic device 101, instead of the main processor 121 while the main processor 121 is in an inactive (e.g., sleep) state or along with the main processor 121 while the main processor 121 is an active state (e.g., executing an application). According to an example embodiment, the auxiliary processor 123 (e.g., an ISP or a CP) may be implemented as a portion of another component (e.g., the camera module 180 or the communication module 190) that may be functionally related to the auxiliary processor 123. According to another example embodiment, the auxiliary processor 123 (e.g., an NPU) may include a hardware structure specified for artificial intelligence model processing. An artificial intelligence model may be generated by machine learning. Such learning may be performed by, for example, the electronic device 101 in which an artificial intelligence model is executed, or performed via a separate server (e.g., the server 108). Learning algorithms may include, but are not limited to, for example, supervised learning, unsupervised learning, semi-supervised learning, reinforcement learning, and the like. The artificial intelligence model may include a plurality of artificial neural network layers. An artificial neural network may include, but is not limited to, a deep neural network (DNN), a convolutional neural network (CNN), a recurrent neural network (RNN), a restricted Boltzmann machine (RBM), a deep belief network (DBN), and a bidirectional recurrent deep neural network (BRDNN), a deep Q-network, or a combination of two or more thereof. The artificial intelligence model may additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. According to an embodiment, the memory 130 may include the volatile memory 132 or the non-volatile memory 134. The non-volatile memory 134 may include an internal memory 136 and an external memory 138.

The program 140 may be stored as software in the memory 130, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), a digital pen (e.g., a stylus pen), and the like.

The sound output module 155 may output a sound signal to the outside of the electronic device 101. According to an example embodiment, the sound output module 155 may include, but is not limited to, a speaker or a receiver. The speaker may be used for general purposes, such as playing multimedia or playing record. The receiver may be used to receive an incoming call. According to another example embodiment, the receiver may be implemented separately from the speaker or as a part of the speaker.

The display module 160 may visually provide information to the outside (e.g., a user) of the electronic device 101. According to an embodiment, the display module 160 may include, for example, a control circuit for controlling a display, a hologram device, or a projector and control circuitry to control a corresponding one of the display, the hologram device, and the projector. According to another example embodiment, the display module 160 may include a touch sensor adapted to detect a touch, or a pressure sensor adapted to measure the intensity of force incurred by the touch.

The audio module 170 may convert a sound into an electrical signal or vice versa. According to an example embodiment, the audio module 170 may obtain the sound via the input module 150 or output the sound via the sound output module 155 or an external electronic device (e.g., the electronic device 102 such as a speaker or a headphone) directly or wirelessly connected to the electronic device 101.

The sensor module 176 may detect an operational state (e.g., power or temperature) of the electronic device 101 or an environmental state (e.g., a state of a user) external to the electronic device 101, and generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support at least one specified protocol to be used for the electronic device 101 to be coupled with the external electronic device (e.g., the electronic device 102) directly (e.g., by wire) or wirelessly. According to an example embodiment, the interface 177 may include, for example, a high-definition multimedia interface (HDMI), a universal serial bus (USB) interface, a secure digital (SD) card interface, an audio interface, and the like.

The connecting terminal 178 may include a connector via in which the electronic device 101 may be physically connected to an external electronic device (e.g., the electronic device 102). According to an example embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or an electrical stimulus that may be recognized by a user via his or her tactile sensation or kinesthetic sensation. According to an example embodiment, the haptic module 179 may include, but is not limited to, a motor, a piezoelectric element, or an electric stimulator.

The camera module 180 may capture a still image and moving images. According to an example embodiment, the camera module 180 may include one or more lenses, image sensors, image signal processors, or flashes.

The power management module 188 may manage power supplied to the electronic device 101. The power management module 188 may be implemented as, for example, at least a part of a power management integrated circuit (PMIC).

The battery 189 may supply power to at least one component of the electronic device 101. According to an example embodiment, the battery 189 may include, but is not limited to, a primary cell that is not rechargeable, a secondary cell that is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel According to an embodiment, the communication module 190 may include at least one communication processor that may be operable independently of the processor 120 (e.g., an AP) and that support a direct (e.g., wired) communication or a wireless communication. According to another embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module, or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a fifth generation (5G) network, a next-generation communication network, the Internet, or a computer network (e.g., a LAN or a wide area network (WAN))). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The wireless communication module 192 may be configured to support a 5G network after a fourth generation (4G) network, and a next-generation communication technology, e.g., a new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., a millimeter wave (mmWave) band) to achieve, e.g., a high data transmission rate. According to an embodiment, the wireless communication module 192 may support various technologies for securing performance on a high-frequency band, such as, e.g., beamforming, massive multiple-input and multiple-output (MIMO), full dimensional MIMO (FD-MIMO), an array antenna, analog beam-forming, or a large scale antenna. The wireless communication module 192 may support various requirements specified in the electronic device 101, an external electronic device (e.g., the electronic device 104), or a network system (e.g., the second network 199). According to another embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an example embodiment, the antenna module 197 may include an antenna including a radiating element including a conductive material or a conductive pattern formed in or on a substrate (e.g., a printed circuit board (PCB)). According to another example embodiment, the antenna module 197 may include a plurality of antennas (e.g., array antennas). In such a case, at least one antenna appropriate for a communication scheme used in a communication network, such as the first network 198 or the second network 199, may be selected by, for example, the communication module 190 from the plurality of antennas. The signal or the power may be transmitted or received between the communication module 190 and the external electronic device via the at least one selected antenna. According to an example embodiment, another component (e.g., a radio frequency integrated circuit (RFIC)) other than the radiating element may be additionally formed as a part of the antenna module 197.

According to various example embodiments, the antenna module 197 may form a mmWave antenna module. According to an embodiment, the mmWave antenna module may include a PCB, an RFIC disposed on a first surface (e.g., a bottom surface) of the PCB or adjacent to the first surface and capable of supporting a designated high-frequency band (e.g., the mmWave band), and a plurality of antennas (e.g., array antennas) disposed on a second surface (e.g., a top or a side surface) of the PCB, or adjacent to the second surface and capable of transmitting or receiving signals in the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an example embodiment, commands or data may be transmitted or received between the electronic device 101 and the external electronic device 104 via the server 108 coupled with the second network 199. Each of the external electronic devices 102 or 104 may be a device of the same type as or a different type from the electronic device 101. According to another example embodiment, all or some of operations to be executed by the electronic device 101 may be executed at one or more of the external electronic devices 102 and 104, and the server 108. For example, if the electronic device 101 needs to perform a function or a service automatically, or in response to a request from a user or another device, the electronic device 101, instead of, or in addition to, executing the function or the service, may request at least one external electronic device to perform at least part of the function or the service. The at least one external electronic device receiving the request may perform the at least part of the function or the service requested, or an additional function or an additional service related to the request, and may transfer an outcome of the performing to the electronic device 101. In an example embodiment, the electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another example embodiment, the external electronic device 104 may include an Internet-of-things (IoT) device. The server 108 may be an intelligent server using machine learning and/or a neural network.

According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
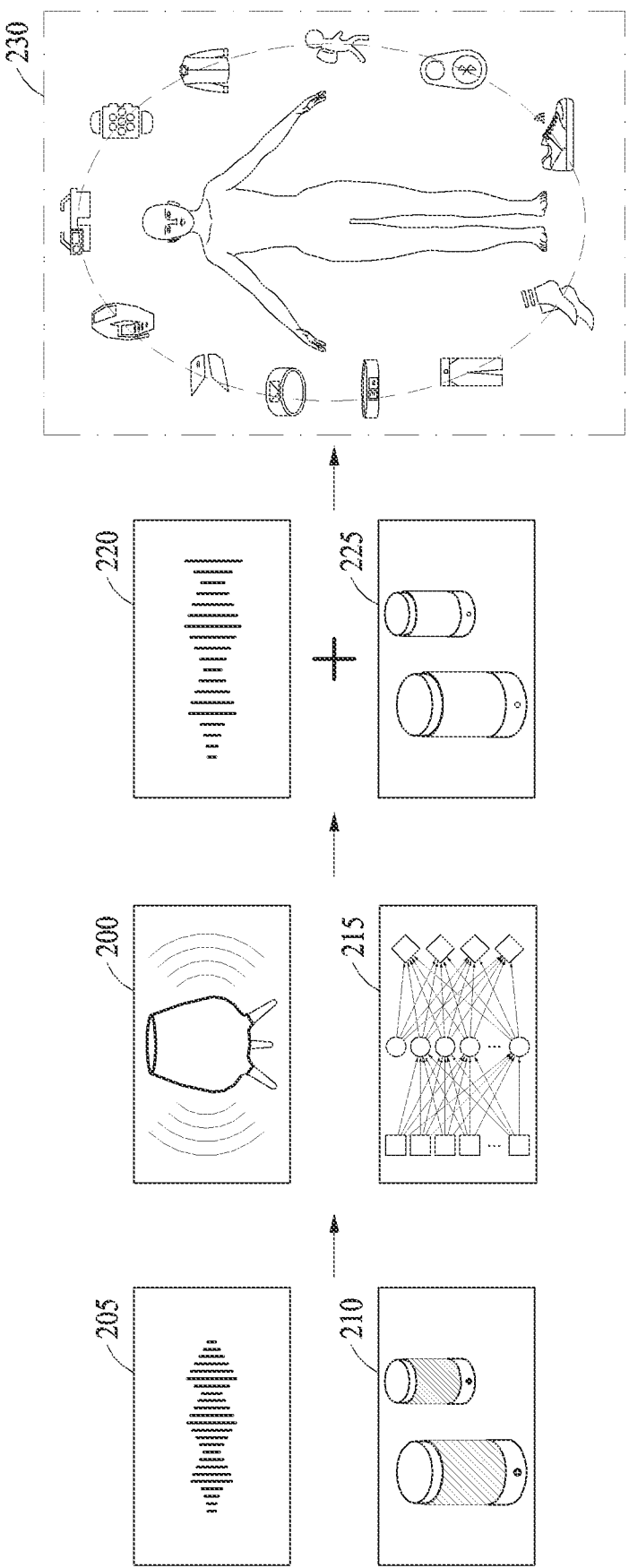
FIG. 2 is a diagram illustrating a method of providing audiovisual content for the disabled, according to an embodiment of the disclosure.

FIG. 2 is a diagram illustrating a method of providing audiovisual content for the disabled, according to an embodiment of the disclosure.

An electronic device 200 (e.g., the electronic device 101 of FIG. 1), such as an artificial intelligence (AI) speaker, a television (TV), and a terminal device, may recommend or provide visual content 205 and audio content 210 to a user through an IoT device. In one embodiment, the IoT device may include various IoT devices, such as a wearable device, a mobile device, an IoT home appliance, and the like.

For example, the electronic device 200 may express the weather by using the audiovisual contents 205 and 210, such as lighting in a cool color in snowy weather, an image of snow falling, sound of stepping on snow, related music, and autonomous sensory meridian response (ASMR) content depending on the weather, and the user may identify the weather by watching and listening to the content.

In a case in which the user has audiovisual impairment, the user may have a sense that the user does not perceive because of impairment and may have a difficulty in completely recognizing the audiovisual contents 205 and 210.

To allow a user with audiovisual impairment to feel the same level of sensibility as a non-disabled person, converted contents 220 and 225, which are a conversion into the sense that the user with audiovisual impairment may feel, may be needed.

According to an embodiment, the electronic device 200 may collect context information on a user and may provide the audiovisual contents 220 and 225 preferred and perceptible by the user to reflect the preference of the user.

The context information may include information on a user and a surrounding environment of the user, such as a usage history of an IoT device, a usage history of accessibility improvement of the IoT device, a command history utilizing a speaker of the IoT device, a usage habit of the IoT device, a current state of the IoT device, information provided or supplied by the user, biometric information of the user, voice information of the user, an image capturing the user, date, day, time, weather, birthday of the user, and the like. According to another embodiment, the user may directly input information on an impairment state of the user to the electronic device 200 or the information on an impairment state of the user may be estimated based on the usage history of the IoT device and the usage habit of the IoT device.

For example, the context information may include the information provided or supplied by the user, such as a disability state of the user, an activity of a mobile device of the user, played music, a visited place, a picture captured by the user, a message, and social network service (SNS) activity, a usage history of an accessibility improvement function, such as a high contrast mode of the IoT device, a usage history of the IoT device, such as TV content watched by the user, a state of lighting of a surrounding IoT device depending on the weather, and a current state of the IoT device, such as a state of a display device.

In another example, the electronic device 200 may convert the audiovisual contents 205 and 210, based on environment information (e.g., the weather) around the user, for a general user into the audiovisual contents 220 and 225 for the disabled, based on the audiovisual impairment state of the user and preference, and may output the converted audiovisual contents 220 and 225 for the disabled through an IoT device 230 around the user.

According to an embodiment, in a case in which the user has visual impairment, an electronic device may output the audiovisual contents 205 and 210 for a general user by an audio type 220. According to another embodiment, in a case in which the user has audio impairment, the electronic device 200 may output the audiovisual contents 205 and 210 for a general user by changing a color of lighting 225 and text by utilizing at least one of a mobile device, a smart device, a TV, or a lighting device mounted on the TV or any combination thereof, connected to the electronic device.

The electronic device 200 may visually and audibly express information on the environment around a user, such as the weather, and may provide an emotional experience perceptible by the user based on the audiovisual impairment state by using emotional sound, music, lighting, and an image. According to an embodiment, the electronic device 200 may estimate an emotion of the user and may provide emotional sound, music, lighting, and an image corresponding to the estimated emotion.

The electronic device 200 may output the current state of the IoT device around the user by a form perceptible by the user.

According to another embodiment, the electronic device 200 may output an important notification and alert, such as a fire alert, by a form perceptible by the user, based on the audiovisual impairment state.

FIG. 2 illustrates a process of converting the audiovisual contents 205 and 210 for a general user into the audiovisual contents 220 and 225 for the disabled and outputting the audiovisual contents 220 and 225 for the disabled to the IoT device 230 around the user.

As an example, the electronic device 200 may collect current weather information and may determine the audiovisual contents 205 and 210 for a general user to provide to the user, based on at least one of the context information stored for the user and the collected weather information.

The electronic device 200 may convert the audiovisual contents 220 and 215 for a general user into the audiovisual contents 205 and 210 for the disabled based on the impairment state of the user by using a deep learning model 215.

The electronic device 200 may classify an audiovisual IoT device around a user among one or more IoT devices 230 connected to the electronic device 200 and may output the converted audiovisual contents 205 and 210 for the disabled on the audiovisual IoT devices. The electronic device 200 may reschedule the one or more IoT devices 230 connected to the electronic device 200.

According to an embodiment, the electronic device 200 may determine the audiovisual contents 205 and 210 for a disabled to output by performing training the deep learning model 215 on the context information on the user and the surrounding environment of the user, such as the local weather of the user. According to another embodiment, the electronic device 200 may receive feedback of the user on the output audiovisual contents 205 and 210 for the disabled, may train a deep learning model 215 by using the feedback, and may use the trained deep learning model 215 to determine the audiovisual contents 205 and 210 for the disabled to output.

Hereinafter, a method of providing audiovisual content is described with reference to FIG. 3.

Figure 3:
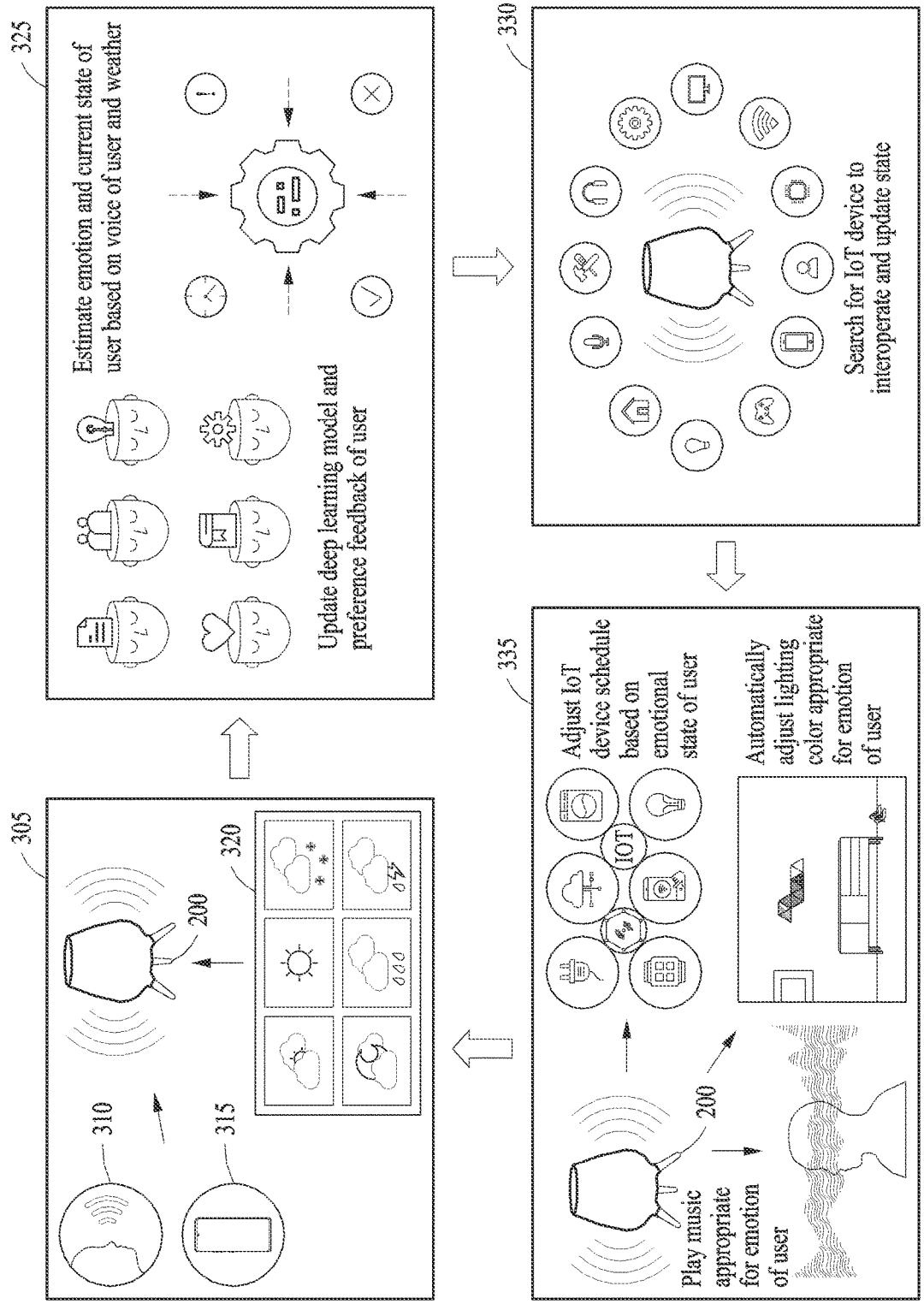
FIG. 3 is a diagram illustrating an operation of a method of providing audiovisual content for the disabled, according to an embodiment of the disclosure.

FIG. 3 is a diagram illustrating an operation of a method of providing audiovisual content for a disabled, according to an embodiment of the disclosure.

Referring to FIG. 3, in operation 305, an electronic device 200 may detect an occurrence of a trigger event based on an input 310 to the electronic device 200 and an input 315 to at least one IoT device connected to the electronic device 200. The input 310 to the electronic device 200 and the input 315 to the at least one IoT device connected to the electronic device 200 may include various inputs such as a voice input of a user for the electronic device 200 and the at least one IoT device connected to the electronic device 200, a touch input, a user's motion sensed by the at least one IoT device, and a user's biometric signal sensed by a sensor of the at least one IoT device.

According to an embodiment, the electronic device 200 may collect weather information 320 in response to the occurrence of the trigger event.

In operation 325, the electronic device 200 may estimate at least one of an emotion of the user and an audiovisual impairment state of the user, based on at least one of context information stored for the user and the weather information 320. The audiovisual impairment state may be input by the user or may be estimated by a usage history and a usage habit of the IoT device of the user (e.g., a history of activating an accessibility function of the IoT device). In a case in which the context information on the user includes the audiovisual impairment state of the user as the user inputs the impairment state, the audiovisual impairment state included in the context information may be estimated as the audiovisual impairment state of the user.

Operation 325 of estimating the emotion may be performed by using a trained deep learning model. For example, the deep learning model may be a deep learning model trained to output audiovisual content for the disabled based on at least one of the context information (e.g., information on the user and a surrounding environment of the user, such as a usage history of an IoT device, a usage habit of an IoT device, an impairment state of the user, voice information of the user, and an image capturing the user), the weather information 320, and the like. The deep learning model may be further trained with preference feedback of the user on the audiovisual content for the disabled.

The deep learning model may include an artificial neural network for estimating the emotion of the user and a look-up table (LUT) indicating a correlation among the estimated emotion, the weather information, and audiovisual content, and the like, for a general user. The LUT may be an LUT that indicates a correlation between audiovisual content and at least one of an estimated emotional state of the user, an impairment state of the user, and the weather information 320, and may be a model file storing a parameter relationship of the artificial neural network. The deep learning model may further include a plurality of LUTs.

In operation 325, the electronic device 200 may determine audiovisual contents for a general user by using at least one of the estimated emotion of the user and the weather information 320 and may determine audiovisual content for the disabled based on the audiovisual contents for a general user.

Among the audiovisual contents for a general user, the electronic device 200 may determine audiovisual content for a general user perceptible by the user based on the audiovisual impairment state. In an embodiment, the electronic device 200 may determine the audiovisual content for the disabled based on the audiovisual content perceptible by the user. The electronic device 200 may convert the audiovisual content, perceptible by the user, for a general user into content that the user may better perceive and may determine the audiovisual content for the disabled, based on the converted content.

For example, in a case in which the user has visual impairment, between image content and music content, the user may not completely perceive the image content. The electronic device 200 may determine the audiovisual content for the disabled based on the music content perceptible by the user, based on the visual impairment state of the user. In another case in which the user has visual impairment and dull auditory sense, the electronic device 200 may determine the audiovisual content for the disabled by music content increasing a volume level to be perceptible by the user, based on music content for a general user.

In operation 330, the electronic device 200 may find at least one audiovisual IoT device interoperable with the electronic device 200 and may update a state of the audiovisual IoT device to a state in which the audiovisual content for the disabled may be output. In an embodiment, the electronic device 200 may determine a target IoT device to output the audiovisual content for the disabled, which may be determined in operation 325, among the at least one IoT device connected to the electronic device 200.

According to an embodiment, the electronic device 200 may determine a location of the user by utilizing the at least one IoT device connected to the electronic device 200 and may identify an IoT device around the user based on the determined location of the user. The electronic device 200 may identify an IoT device corresponding to the location of the user, based on a retention list of IoT devices of the user. The electronic device 200 may determine the target IoT device based on the identified IoT device.

According to another embodiment, the electronic device 200 may identify an attribute of the at least one IoT device connected to the electronic device 200 and may classify an audiovisual IoT device among the at least one IoT device, based on the identified attribute.

The electronic device 200 may determine the target IoT device to output the determined audiovisual content for the disabled, based on the attribute of the classified audiovisual IoT device and the trigger event.

In operation 335, the electronic device 200 may output the audiovisual content for the disabled, which may be determined in operation 325, through the IoT device classified in operation 330. For example, in a situation in which the audiovisual content for the disabled is lighting content, the electronic device 200 may output the lighting content to an IoT device that may output lighting, and in a situation in which the audiovisual content for the disabled is music, the electronic device 200 may output the music through an IoT device that may output music.

For example, when the user with visual impairment watches a TV by performing operations 305, 325, 330, and 335, the electronic device 200 may convert surrounding environment information (e.g., the weather) into a deliverable state to the user with visual impairment through the TV and may deliver the surrounding environment information through sound related to the weather, image, sign language, and lighting mounted on the TV, in response to the trigger event.

According to another embodiment, the electronic device 200 may identify whether the user is using a mobile device by identifying an input of the mobile device connected to the electronic device 200 or a usage state of an application executed by the mobile device and may provide visual or auditory notification to the user through a wearable device synced with the mobile device, such as wireless earphones and a smart watch.

The electronic device 200 may adjust a schedule of IoT devices around the user based on the obtained weather information 320 and the emotion and impairment state of the user, which are estimated in operation 325.

According to yet another embodiment, the electronic device 200 may receive a preference feedback of the user on the output audiovisual content for the disabled. The preference feedback may include explicit feedback that the user explicitly expresses preference to the audiovisual content and implicit feedback originated from an action of the user, such as frequently using the audiovisual content and turning off the audiovisual content.

The electronic device 200 may learn the preference feedback of the user by using a deep learning model trained to output the audiovisual content for the disabled, based on the context information stored for the user and the weather information 320, and may update the deep learning model.

The electronic device 200 may wait until a next trigger event occurs and in a case in which the next trigger event has occurred, the electronic device 200 may provide the audiovisual content for the disabled by using the updated deep learning model.

Hereinafter, the deep learning model is described with reference to FIG. 4.

Figure 4:
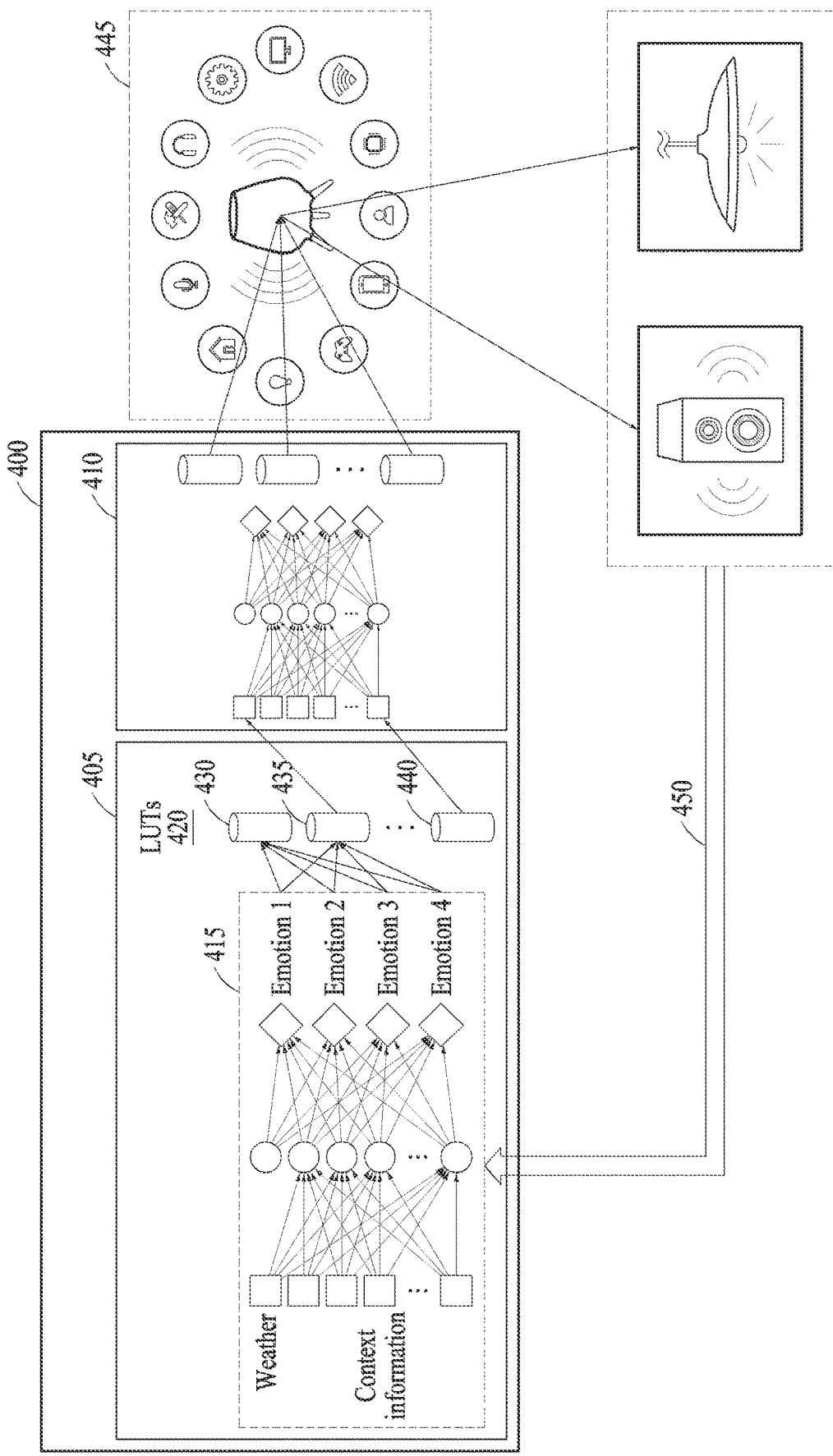
FIG. 4 is a diagram illustrating a deep learning model used for a method of providing audiovisual content for the disabled, according to an embodiment of the disclosure.

FIG. 4 is a diagram illustrating a deep learning model used for a method of providing audiovisual content for a disabled, according to an embodiment of the disclosure.

FIG. 4 illustrates an electronic device 200 and a deep learning model 400 used for a method of providing audiovisual content for the disabled. According to an embodiment, the electronic device 200 may output audiovisual content for the disabled through the deep learning model 400, based on at least one of context information stored for a user and weather information.

The deep learning model 400 may include a first deep learning model 405 configured to output audiovisual content for a general user, based on at least one of context information on the user and weather information, and a second deep learning model 410 configured to output audiovisual content for the disabled based on an output of the first deep learning model 405.

The first deep learning model 405 may include an artificial neural network 415 configured to estimate an emotion of the user and LUTs 420 indicating a correlation among the estimated emotion, weather information, and the audiovisual content for a general user. The LUTs 420 may be an LUT indicating a correlation between audiovisual content and at least one of an estimated emotional state of the user, an audiovisual impairment state of the user, and the weather information 320, and may be a model file storing a parameter relationship of the artificial neural network.

The artificial neural network 415 of the first deep learning model 405 may be the artificial neural network 415 trained to estimate the emotion of the user by an input based on the context information stored for the user and the weather information.

The first deep learning model 405 may include the LUTs 420 indicating a correlation among the estimated emotion, weather information, and audiovisual content for a general user. The first deep learning model 405 may include LUTs 430, 435, and 440 indicating correlations among lighting content, music content, image content, estimated emotion of the user, and the weather information. However, the example need not be limited thereto. The LUTs 420 included in the first deep learning model 405 may indicate a correlation among various audiovisual contents, emotion, and weather information. The electronic device 200 may determine the audiovisual content for a general user by using the artificial neural network 415 of the first deep learning model 405 and the LUTs 420.

In an embodiment, the deep learning model 400 may include the second deep learning model 410 configured to output the audiovisual content for the disabled, based on an output of the first deep learning model 405.

In a case in which the user has visual impairment, the user may not completely perceive audiovisual contents included in the LUTs 420 of the first deep learning model 405. Among the audiovisual contents for a general user determined through the first deep learning model 405, the electronic device 200 may determine audiovisual content for a general user (e.g., the audiovisual contents of the LUTs 435 and 440) perceptible by the user depending on the audiovisual impairment state.

Even though the user may perceive the audiovisual content for a general user, an audiovisual disabled person may not perceive the content at the same level as a general user. For example, although a visually impaired person may perceive text content, the visually impaired person may have a difficulty in understanding the content when the visually impaired person has poor sight.

The electronic device 200 may determine audiovisual content for the disabled easily perceptible by the user, based on the audiovisual content for a general user (e.g., the audiovisual contents of the LUTs 435 and 440) perceptible by the user, through the second deep learning model 410.

Among the audiovisual contents for a general user determined by the first deep learning model 405, the audiovisual contents for a general user perceptible by the user depending on the audiovisual impairment state of the user may be input to the second deep learning model 410. The second deep learning model 410 may output the audiovisual content for the disabled based on the input audiovisual contents for a general user.

The second deep learning model 410 may be a modified model of the first deep learning model 405. Since some senses of an audiovisual impaired person are dull, based on designing a new deep learning model for determining audiovisual content for the disabled by using context information on the user and weather information, the structure thereof may be different from the deep learning model for a general user and may cost high. The electronic device 200 may provide appropriate content to the disabled at low cost by determining audiovisual content for the disabled from audiovisual content for a general user by using the second deep learning model 410 modified from the first deep learning model 405 that generates the audiovisual content for a general user.

According to an embodiment, the electronic device 200 may output the audiovisual content for the disabled determined by using the deep learning model 400 through at least one IoT device 445 connected to the electronic device 200.

The electronic device 200 may train the second deep learning model 410 again by receiving preference feedback 450 of the user for the output audiovisual content for the disabled. The preference feedback 450 may include explicit feedback that the user explicitly expresses preference to the audiovisual content and implicit feedback originated from an action of the user, such as frequently using the audiovisual content and turning off the audiovisual content.

The electronic device 200 may provide more suitable audiovisual content to the user by learning the preference feedback 450 of the user.

The first deep learning model 405 and the second deep learning model 410 may be replaced with an LUT indicating a correlation between an input and an output of each model. The deep learning model 400 may be replaced with an LUT indicating a correlation between an input and an output of the model. The first deep learning model 405 and the second deep learning model 410 may be integrated as one deep learning model.

Since the electronic device 200 provides the audiovisual content for the disabled by using the deep learning model 400 and LUTs corresponding to the deep learning model 400, the user may easily understand information provided by the electronic device 200.

The electronic device 200 may visually and audibly express information on the environment around the user, such as the weather, and may provide an emotional experience to the user by utilizing emotional sound, music, lighting, and an image.

According to an embodiment, in a situation in which a user with visual impairment inputs a voice command, "How is the wind today?" to the electronic device 200, the electronic device 200 may provide a realistic and emotional experience by outputting a response in a special audio effect corresponding to wind speed or in a voice through a speaker of the electronic device 200 by using the deep learning model 400 and/or the LUT corresponding to the deep learning model 400. In a situation in which a user with hearing impairment inputs a voice command, "How is the wind today?" to the electronic device 200, the electronic device 200 may change a color of a lighting device at home by an animated lighting pattern in a direction that is the same as the direction of the wind through the IoT device 445 connected to the electronic device 200 by using the deep learning model 400 and/or the LUT corresponding to the deep learning model 400.

For example, when a user with light visual impairment requests the electronic device 200 to play music, the electronic device 200 may play the music through the speaker of the electronic device 200 and may improve the emotional experience of the user by displaying an appropriate music or pattern by using the IoT device 445 connected to the electronic device 200.

In another example, when the electronic device 200 estimates that the user is excited, the electronic device 200 may recommend exciting music to the user with visual impairment or may provide colorful lighting content to the user with hearing impairment.

Figure 5:
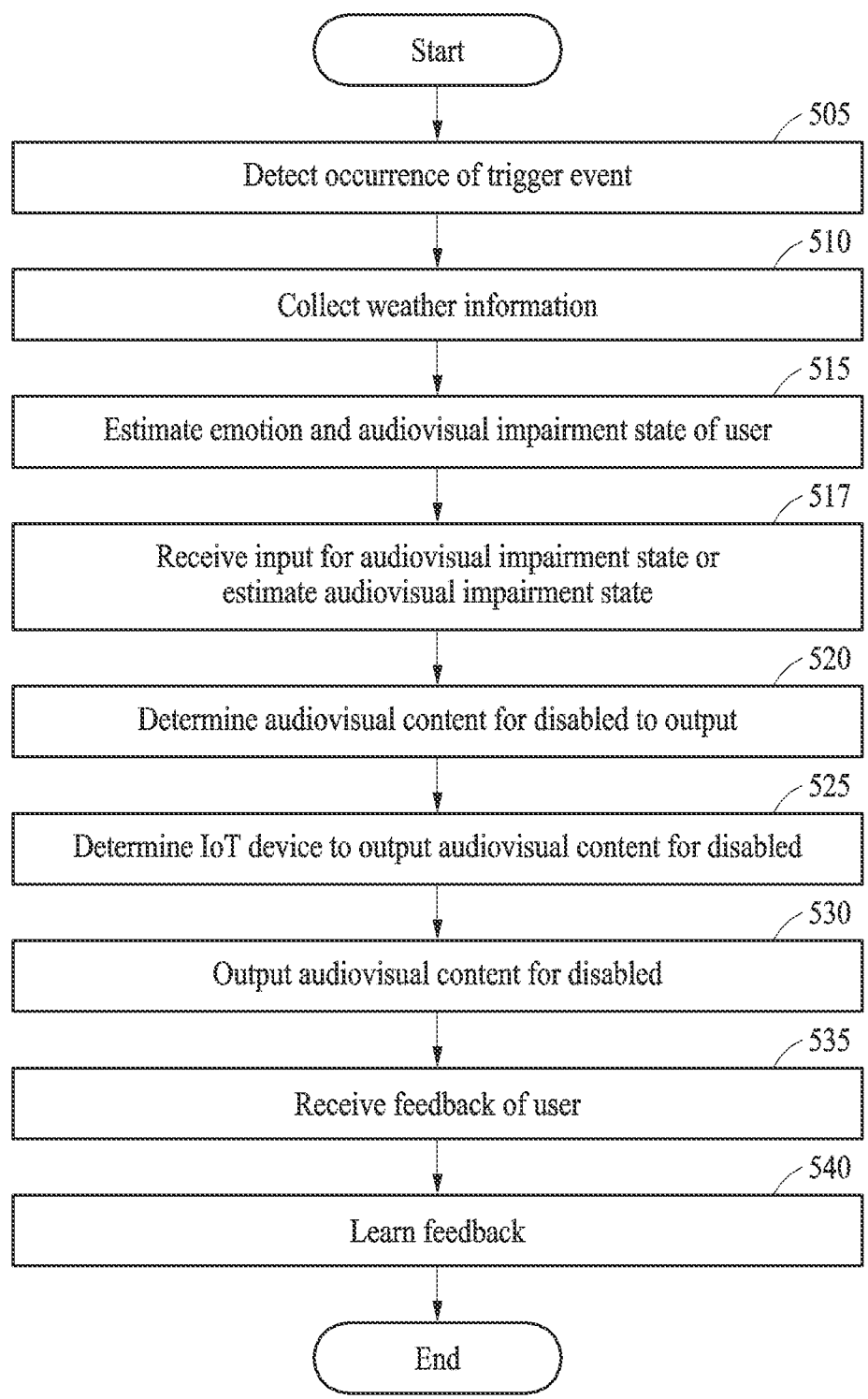
FIG. 5 is a flowchart illustrating a method of providing audiovisual content for the disabled, according to an embodiment of the disclosure.

FIG. 5 is a flowchart illustrating a method of providing audiovisual content for the disabled, according to an embodiment of the disclosure.

Referring to FIG. 5, in operation 505, an electronic device 200 may detect an occurrence of a trigger event, based on an input to the electronic device 200 and an input to at least one IoT device connected to the electronic device 200. The input to the electronic device 200 and the input to at least one IoT device connected to the electronic device 200 may include various inputs such as a voice input of the user to the electronic device 200 and the at least one IoT device connected to the electronic device 200, a touch input, a user's motion sensed by the at least one IoT device, a user's biometric signal sensed by the at least one IoT device, and the like.

For example, the electronic device 200 may sense that the user may be excited based on a biometric signal measured by a wearable device connected to the electronic device 200. In a case in which the electronic device 200 senses that the user is excited, the electronic device 200 may sense that the trigger event has occurred.

When the electronic device 200 receives a voice command of the user, the electronic device 200 may sense that the trigger event has occurred.

In another case, when the electronic device 200 senses that the user woke up by a user's touch input to the electronic device 200, the electronic device 200 may sense that the trigger event has occurred.

When weather information periodically input to the electronic device 200 includes a weather warning, the electronic device 200 may sense that the trigger event has occurred.

However, the trigger event need not be limited thereto and may be set in various ways as needed.

In operation 510, the electronic device 200 may collect weather information in response to the occurrence of the trigger event.

In operation 515, the electronic device 200 may estimate an emotion of the user, based on at least one of context information stored for the user and the weather information.

The electronic device 200 may estimate an emotional state of the user by analyzing a usage history and a usage habit of the IoT device of the user (e.g., a history of activating an accessibility function of the IoT device).

In operation 517, the electronic device 200 may receive an audiovisual impairment state of the user from the user or may estimate the audiovisual impairment state based on the context information stored for the user.

For example, the electronic device 200 may receive an input for the audiovisual impairment state from the user. In a case in which the context information, which is previously input by the user, for the user includes the audiovisual impairment state of the user, the electronic device 200 may estimate the audiovisual impairment state of the user by the audiovisual impairment state included in the context information. The audiovisual impairment state may be estimated by a usage history and a usage habit of the IoT device of the user (e.g., a history of activating an accessibility function of the IoT device).

The operation of estimating the emotion in operation 515 may be performed by using an artificial neural network (e.g., the artificial neural network 415 of FIG. 4) of a trained first deep learning model (e.g., the first deep learning model 405 of FIG. 4). The description of the first deep learning model has been provided with reference to FIG. 4, and thus, any repeated description may be omitted. Instead of an artificial neural network of the trained first deep learning model, the operation of estimating the emotion in operation 515 may be performed by using an LUT corresponding to the artificial neural network.

In operation 520, the electronic device 200 may determine audiovisual content for the disabled to output, based on at least one of the emotion estimated in operation 515 and the audiovisual impairment state determined in operation 517. The electronic device 200 may determine the audiovisual content for the disabled to output by further using weather information.

The electronic device 200 may determine audiovisual content for a general user, based on the weather information and the estimated emotion. The operation of determining the audiovisual content for a general user, based on the weather information and the estimated emotion, may be, for example, performed by using LUTs (e.g., the LUTs 420 of FIG. 4) of the first deep learning model.

Among the audiovisual content for a general user, the electronic device 200 may determine audiovisual content for a general user perceptible by a user based on the audiovisual impairment state.

The electronic device 200 may determine the audiovisual content for the disabled based on the determined audiovisual content for a general user. The electronic device 200 may convert the audiovisual content, perceptible by the user, for a general user into content that the user may better perceive through a second deep learning model (e.g., the second deep learning model 410 of FIG. 4) and may determine the audiovisual content for the disabled based on the converted content.

In operation 525, the electronic device 200 may determine a target IoT device to output the determined audiovisual content for the disabled among the at least one IoT device connected to the electronic device 200.

In an example, the electronic device 200 may determine a location of the user by using the at least one IoT device connected to the electronic device 200 and may identify an IoT device around the user based on the determined location of the user. In another example, the electronic device 200 may determine a location of the user by recognizing the user by a sensor of the at least one IoT device connected to the electronic device 200.

The electronic device 200 may identify an IoT device corresponding to the location of the user, based on a retention list of IoT devices of the user. The electronic device 200 may determine the target IoT device based on the identified IoT device.

The electronic device 200 may identify an attribute of the at least one IoT device connected to the electronic device 200 and may classify an audiovisual IoT device among the at least one IoT device, based on the identified attribute.

An attribute corresponding to a function of the IoT device connected to the electronic device 200 may be defined by the electronic device 200 or may be input by the user. A switch attribute for turning on and off a lighting device for an IoT device including the lighting device, a switch level attribute for controlling brightness of the lighting device, and a color temperature attribute for controlling a color temperature of the lighting device may be defined or input. However, this is an example, and various attributes for various IoT devices may be defined or input as needed.

The electronic device 200 may determine a target IoT device to output the audiovisual content for the disable, based on the classified attribute of the audiovisual IoT device and the trigger event. In a case in which the audiovisual content for the disabled is visual content, the electronic device 200 may determine the target IoT device by an audiovisual IoT device that may play the visual content. In a case in which the user requests to play music through a voice command, the electronic device 200 may determine the target IoT device by an audiovisual IoT device that may play the music.

The electronic device 200 may determine a location of a user by using the at least one IoT device connected to the electronic device 200 and may identify at least one IoT device around the user based on the determined location of the user. The electronic device 200 may identify the at least one IoT device corresponding to the location determined based on a retention list of the IoT device of the user. The electronic device 200 may determine the target IoT device among the identified at least one IoT device. The electronic device 200 may determine the target IoT device by considering attributes of the identified at least one IoT device.

In operation 530, the electronic device 200 may output, through the target IoT device, the audiovisual content for the disabled determined in operation 525. The electronic device 200, for example, may receive preference feedback of the user for not only the audiovisual content output in operation 530 but also other audiovisual contents output through the IoT devices connected to the electronic device 200.

In operation 535, the electronic device 200 may receive the preference feedback of the user. In operation 540, the electronic device 200 may update the second deep learning model by learning the received preference feedback. The electronic device 200 may learn the preference feedback of the user on not only the audiovisual content output in operation 530 but also other audiovisual contents output through the IoT devices connected to the electronic device 200.

Figure 6:
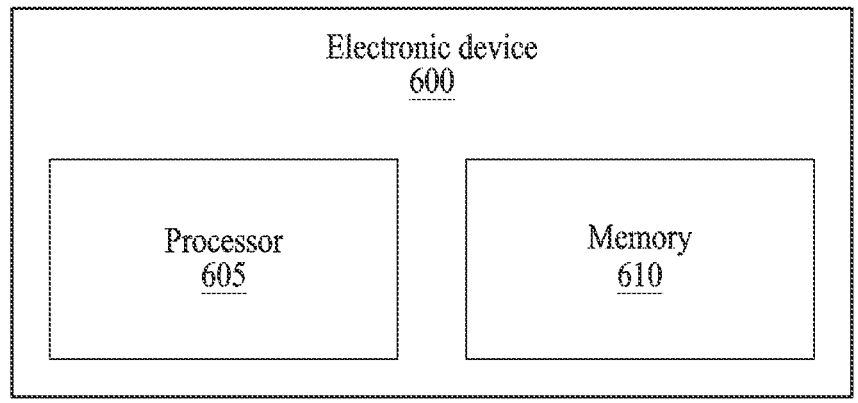
FIG. 6 is a block diagram illustrating an example of an electronic device according to an embodiment of the disclosure.

FIG. 6 is a block diagram illustrating an example of an electronic device according to an embodiment of the disclosure.

Referring to FIG. 6, an electronic device 600 (e.g., the electronic device 200 of FIG. 2) may include a processor 605, and at least one memory 610 configured to store instructions executable by the processor 605, wherein, in a case in which the instructions are executed by the processor 605, the processor 605 may be configured perform sensing an occurrence of a trigger event, based on an input to the electronic device 600 and an input to at least one Internet of Things (IoT) device (e.g., the IoT device 445 of FIG. 4) connected to the electronic device, collecting weather information in response to the occurrence of the trigger event, estimating an emotion of a user, based on at least one of context information stored for the user and the weather information, receiving, from the user, an audiovisual impairment state of the user or estimating the audiovisual impairment state based on the context information, determining audiovisual content for the disabled to output, based on at least one of the estimated emotion and the audiovisual impairment state, among the at least one IoT device, determining a target IoT device to output the determined audiovisual content for the disabled, and outputting the determined audiovisual content for the disabled through the target IoT device.

The determining of the target IoT device may include determining a location of the user by using the at least one IoT device connected to the electronic device 600, and identifying the at least one IoT device around the user, based on the determined location of the user.

The identifying of the IoT device may include identifying at least one IoT device corresponding to the determined location, based on a retention list of IoT devices of the user.

In an embodiment, the determining of the audiovisual content for the disabled may include determining the audiovisual content for the disabled to output by further using the weather information.

In another embodiment, the determining of the audiovisual content for the disabled may include determining audiovisual contents for a general user based on the weather information and the estimated emotion, among the audiovisual contents for a general user, determining audiovisual contents for a general user perceptible by the user, based on the audiovisual impairment state of the user, and determining the audiovisual content for the disabled based on the determined audiovisual contents for a general user.

In yet another embodiment, the determining of the audiovisual contents for a general user may be performed by using a first deep learning model (e.g., the first deep learning model 405 of FIG. 4) configured to output the audiovisual contents for a general user, based on the weather information and the estimated emotion.

The determining of the audiovisual content for the disabled based on the determined audiovisual contents for a general user may be performed by using a second deep learning model (e.g., the second deep learning model 410 of FIG. 4) modified from the first deep learning model.

The context information may include a usage history of an accessibility improvement function of the at least one IoT device by the user.

Additionally, the context information may include a biometric signal, of the user, measured by a sensor of the at least one IoT device.

The processor 605, for example, may be further configured to perform receiving preference feedback of the user on the output audiovisual content, and updating the second deep learning model by learning the preference feedback.

The determining of the target IoT device may include identifying an attribute of the at least one IoT device connected to the electronic device 600, and classifying an audiovisual IoT device among the at least one IoT device based on the identified attribute.

The determining of the target IoT device may further include determining the target IoT device to output the determined audiovisual content for the disabled, based on an attribute of the classified audiovisual IoT device and the trigger event.

A method of providing audiovisual content for the disabled may include sensing an occurrence of a trigger event, based on an input to the electronic device 600 and an input to at least one IoT device connected to the electronic device 600, collecting weather information in response to the occurrence of the trigger event, estimating an emotion of a user, based on at least one of context information stored for the user and the weather information, receiving, from the user, an audiovisual impairment state of the user or estimating the audiovisual impairment state based on the context information, determining audiovisual content for the disabled to output, based on at least one of the estimated emotion and the audiovisual impairment state, among the at least one IoT device, determining a target IoT device to output the determined audiovisual content for the disabled, and outputting the determined audiovisual content for the disabled through the determined target IoT device.

The determining of the target IoT device, for example, may include determining a location of the user by using the at least one IoT device connected to the electronic device 600, and identifying the at least one IoT device around the user, based on the determined location of the user.

The identifying of the IoT device may include identifying at least one IoT device corresponding to the determined location, based on a retention list of IoT devices of the user.

In an embodiment, the determining of the audiovisual content for the disabled may include determining the audiovisual content for the disabled to output by further using the weather information.

In another embodiment, the determining of the audiovisual content for the disabled may include determining audiovisual contents for a general user, based on the weather information and the estimated emotion, among the audiovisual contents for a general user, determining audiovisual contents for a general user perceptible by the user, based on the audiovisual impairment state of the user, and determining the audiovisual content for the disabled based on the determined audiovisual contents for a general user.

In yet another embodiment, the determining of the audiovisual contents for a general user may be performed by using a first deep learning model (e.g., the first deep learning model 405 of FIG. 4) configured to output the audiovisual contents for a general user, based on the weather information and the estimated emotion.

In still another embodiment, the determining of the audiovisual content for the disabled based on the determined audiovisual contents for a general user may be performed by using a second deep learning model (e.g., the second deep learning model 410 of FIG. 4) modified from the first deep learning model.

An electronic device (e.g., the electronic device 101 of FIG. 1 or the electronic device 200 of FIG. 2) according to various embodiments of the disclosure may be one of various types of electronic devices. The electronic device may include a portable communication device (e.g., a smartphone), a computer device, a portable multimedia device, a portable medical device, a camera, a wearable device, an IoT device, a home appliance device, and the like.

It should be understood that various embodiments of the disclosure and the terms used therein are not intended to limit the technological features set forth herein to particular embodiments and include various changes, equivalents, or replacements for a corresponding embodiment. In connection with the description of the drawings, like reference numerals may be used for similar or related components. As used herein, "A or B", "at least one of A and B", "at least one of A or B", "A, B or C", "at least one of A, B and C", and "A, B, or C," each of which may include any one of the items listed together in the corresponding one of the phrases, or all possible combinations thereof. Terms such as "first", "second", or "first" or "second" may simply be used to distinguish the component from other components in question, and do not limit the components in other aspects (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wired), wirelessly, or via a third element.

As used in connection with various example embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an example embodiment, the module may be implemented in a form of an application-specific integrated circuit (ASIC).

Various embodiments as set forth herein may be implemented as software or machine readable instructions (e.g., the program 140) including one or more instructions that may be stored in a non-transitory storage medium (e.g., the internal memory 136 or the external memory 138) that is readable by a machine (e.g., the electronic device 101) For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data may be semi-permanently stored in the storage medium and where the data may be temporarily stored in the storage medium.

A method according to various example embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various example embodiments, each component (e.g., a module or a program) of the above-described components may include a single entity or multiple entities, and some of the multiple entities may be separately disposed in different components. According to various example embodiments, one or more of the above-described components or operations may be omitted, or one or more other components or operations may be added. Alternatively or additionally, a plurality of components (e.g., modules or programs) may be integrated into a single component. In such a case, according to various example embodiments, the integrated component may still perform one or more functions of each of the plurality of components in the same or similar manner as they are performed by a corresponding one of the plurality of components before the integration. According to various other example embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   at least one processor; and
   at least one memory configured to store instructions executable by the at least one processor,
   wherein, when the instructions are executed by the at least one processor, the at least one processor is configured to perform:
      sensing an occurrence of a trigger event, based on an input to the electronic device and an input to at least one Internet of Things (IoT) device connected to the electronic device,
      collecting weather information in response to the occurrence of the trigger event,
      estimating an emotion of a user, based on at least one of context information stored for the user and the weather information,
      receiving, from the user, an audiovisual impairment state of the user or estimating the audiovisual impairment state based on the context information, determining audiovisual content for a disabled to output, based on at least one of the estimated emotion and the audiovisual impairment state, among the at least one IoT device, determining a target IoT device to output the determined audiovisual content for the disabled, and outputting the determined audiovisual content for the disabled through the target IoT device.

2. The electronic device of claim 1, wherein the determining of the target IoT device comprises:

determining a location of the user by using the at least one IoT device connected to the electronic device, and identifying the at least one IoT device around the user, based on the determined location of the user.

3. The electronic device of claim 2, wherein the identifying of the at least one IoT device comprises identifying at least one IoT device corresponding to the determined location, based on a retention list of IoT devices of the user.

4. The electronic device of claim 1, wherein the determining of the audiovisual content for the disabled comprises determining the audiovisual content for the disabled to output by further using the weather information.

5. The electronic device of claim 4, wherein the determining of the audiovisual content for the disabled comprises:

determining audiovisual contents for a general user based on the weather information and the estimated emotion, among the audiovisual contents for a general user, determining audiovisual contents for a general user perceptible by the user, based on the audiovisual impairment state of the user, and determining the audiovisual content for the disabled based on the determined audiovisual contents for a general user.

6. The electronic device of claim 5, wherein the determining of the audiovisual contents for a general user is performed by using a first deep learning model configured to output the audiovisual contents for a general user, based on the weather information and the estimated emotion.

7. The electronic device of claim 6, wherein the determining of the audiovisual content for the disabled based on the determined audiovisual contents for a general user is performed by using a second deep learning model modified from the first deep learning model.

8. The electronic device of claim 1, wherein the context information comprises a usage history of an accessibility improvement function of the at least one IoT device by the user.

9. The electronic device of claim 1, the context information comprises a biometric signal, of the user, measured by a sensor of the at least one IoT device.

10. The electronic device of claim 7, wherein the at least one processor is further configured to perform:

receiving preference feedback of the user on the output audiovisual content, and updating the second deep learning model by learning the preference feedback.

11. The electronic device of claim 1, wherein the determining of the target IoT device comprises:

identifying an attribute of the at least one IoT device connected to the electronic device, and classifying an audiovisual IoT device among the at least one IoT device based on the identified attribute.

12. The electronic device of claim 11, wherein the determining of the target IoT device comprises determining the target IoT device to output the determined audiovisual content for the disabled, based on an attribute of the classified audiovisual IoT device and the trigger event.

13. A method of providing audiovisual content for a disabled, the method comprising:

sensing an occurrence of a trigger event, based on an input to an electronic device and an input to at least one Internet of Things (IoT) device connected to the electronic device;

collecting weather information in response to the occurrence of the trigger event;

estimating an emotion of a user, based on at least one of context information stored for the user and the weather information;

receiving, from the user, an audiovisual impairment state of the user or estimating the audiovisual impairment state based on the context information;

determining audiovisual content for the disabled to output, based on at least one of the estimated emotion and the audiovisual impairment state;

among the at least one IoT device, determining a target IoT device to output the determined audiovisual content for the disabled; and outputting the determined audiovisual content for the disabled through the determined target IoT device.

14. The method of claim 13, wherein the determining of the target IoT device comprises:

determining a location of the user by using the at least one IoT device connected to the electronic device; and identifying the at least one IoT device around the user, based on the determined location of the user.

15. The method of claim 14, wherein the identifying of the at least one IoT device comprises identifying at least one IoT device corresponding to the determined location, based on a retention list of IoT devices of the user.

16. The method of claim 13, wherein the determining of the audiovisual content for the disabled comprises determining the audiovisual content for the disabled to output by further using the weather information.

17. The method of claim 16, wherein the determining of the audiovisual content for the disabled comprises:

determining audiovisual contents for a general user, based on the weather information and the estimated emotion;

among the audiovisual contents for a general user, determining audiovisual contents for a general user perceptible by the user, based on the audiovisual impairment state of the user; and determining the audiovisual content for the disabled based on the determined audiovisual contents for a general user.

18. The method of claim 17, wherein the determining of the audiovisual contents for a general user is performed by using a first deep learning model configured to output the audiovisual contents for a general user, based on the weather information and the estimated emotion.

19. The method of claim 18, wherein the determining of the audiovisual content for the disabled based on the determined audiovisual contents for a general user is performed by using a second deep learning model modified from the first deep learning model.

20. The method of claim 13, wherein the audiovisual impairment state is based on a usage history and a usage habit of the at least one IoT device of the user.

21. The method of claim 20, wherein the usage habit includes a history of activating an accessibility function of the at least one IoT device of the user.

22. The method of claim 13, further comprising:
converting the weather information and surrounding environment information into a deliverable state.

23. A non-transitory computer-readable storage medium storing instructions that, when executed by a processor, cause the processor to perform the method of claim 13.

* * * * *